(12) United States Patent
Priebe et al.

(10) Patent No.: US 10,703,721 B2
(45) Date of Patent: Jul. 7, 2020

(54) CAFFEIC ACID DERIVATIVES AND USES THEREOF

(71) Applicant: Board of Regents, The University of Texas System, Austin, TX (US)

(72) Inventors: Waldemar Priebe, Houston, TX (US); Stanislaw Skora, Houston, TX (US); Izabela Fokt, Houston, TX (US); Rafal Zielinski, Houston, TX (US); Arumugam Jayakumar, Houston, TX (US); Radjendirane Venugopal, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/185,669

(22) Filed: Nov. 9, 2018

(65) Prior Publication Data

US 2019/0177276 A1 Jun. 13, 2019

Related U.S. Application Data

(60) Provisional application No. 62/584,591, filed on Nov. 10, 2017.

(51) Int. Cl.
| | |
|---|---|
| *C07D 213/57* | (2006.01) |
| *C07D 213/61* | (2006.01) |
| *A61P 35/00* | (2006.01) |
| *A61P 35/02* | (2006.01) |
| *A61K 9/00* | (2006.01) |
| *C07C 57/145* | (2006.01) |

(52) U.S. Cl.
CPC .......... *C07D 213/57* (2013.01); *A61K 9/0014* (2013.01); *A61K 9/0019* (2013.01); *A61K 9/0053* (2013.01); *A61P 35/00* (2018.01); *A61P 35/02* (2018.01); *C07C 57/145* (2013.01); *C07D 213/61* (2013.01)

(58) Field of Classification Search
CPC ............................. C07D 213/57; C07D 213/61
See application file for complete search history.

(56) References Cited

U.S. PATENT DOCUMENTS

| | | |
|---|---|---|
| 6,426,366 B1 | 7/2002 | Novogrodsky et al. |
| 7,745,468 B2 | 6/2010 | Priebe et al. |
| 8,119,827 B2 | 2/2012 | Priebe et al. |
| 8,143,412 B2 | 3/2012 | Priebe et al. |
| 8,637,675 B2 | 1/2014 | Priebe et al. |
| 8,648,102 B2 | 2/2014 | Priebe et al. |
| 8,779,151 B2 | 7/2014 | Priebe et al. |
| 8,809,377 B2 | 8/2014 | Donato et al. |
| 9,000,179 B2 | 4/2015 | Priebe et al. |
| 9,096,499 B2 | 8/2015 | Priebe et al. |
| 9,868,736 B2 | 1/2018 | Donato et al. |
| 2003/0013748 A1 | 1/2003 | Novogrodsky et al. |
| 2010/0292229 A1 | 11/2010 | Donato et al. |
| 2013/0129675 A1 | 5/2013 | Priebe et al. |
| 2014/0357673 A1 | 12/2014 | Donato et al. |
| 2015/0094343 A1 | 4/2015 | Priebe et al. |
| 2017/0095457 A1 | 4/2017 | Lonergan |

FOREIGN PATENT DOCUMENTS

| | | |
|---|---|---|
| WO | WO 1998/006391 | 2/1998 |
| WO | WO 2005/058829 | 6/2005 |
| WO | WO 2007/115269 | 10/2007 |
| WO | WO 2008/005954 | 1/2008 |
| WO | WO 2010/005807 | 1/2010 |
| WO | WO 2011/069141 | 6/2011 |
| WO | WO 2012/040527 | 3/2012 |
| WO | WO 2015/054555 | 4/2015 |
| WO | WO 2015/183987 | 12/2015 |
| WO | WO 2015/187427 | 12/2015 |

OTHER PUBLICATIONS

Alas and Bonavida, "Inhibition of constitutive STAT3 activity sensitizes resistant non-Hodgkin's lymphoma and multiple myeloma to chemotherapeutic drug-mediated apoptosis", *Clin. Cancer Res.*, 9(1):316-326, 2003.

Bharti et al., "Curcumin (diferuloylmethane) inhibits constitutive and IL-6-inducible STAT3 phosphorylation in human multiple myeloma cells", *J. Immunol.*, 171(7):3863-3871, 2003.

Burdelya et al., "Combination Therapy with AG-490 and Interleukin 12 Achieves Greater Antitumor Effects than Either Agent Alone", *Mol. Cancer Ther.*, 1(11):893-899, 2002.

Catlett-Falcone et al., "Constitutive activation of Stat3 signaling confers resistance to apoptosis in human U266 myeloma cells", *Immunity*, 10(1):105-115, 1999.

Constantin et al., "Tyrphostin AG490, a tyrosine kinase inhibitor, blocks actively induced experimental autoimmune encephalomyelitis", *Eur. J. Immunol.*, 28(11):3523-3529, 1998.

Gonzalez-Hernandez et al., "Chemical derivatives of a small molecule deubiquitinase inhibitor have antiviral activity against several RNA viruses", *PLoS One*, 9(4):e94491, 2014.

International Search Report and Written Opinion issued in corresponding PCT Application No. PCT/US2018/059975, dated Feb. 11, 2019.

(Continued)

*Primary Examiner* — Noble E Jarrell
(74) *Attorney, Agent, or Firm* — Parker Highlander PLLC

(57) ABSTRACT

In one aspect, the present disclosure provides caffeic acid derivatives of the formula:

(I)

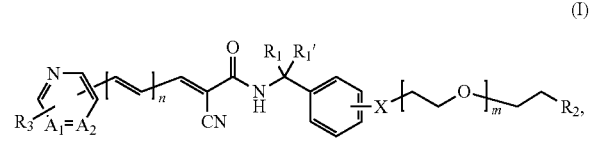

wherein the variables are as defined herein. In another aspect, the present disclosure provides pharmaceutical compositions and methods of using of the compounds disclosed herein, including for the treatment of cancer.

21 Claims, No Drawings

(56) References Cited

OTHER PUBLICATIONS

Iwamaru et al., "A novel inhibitor of the STAT3 pathway induces apoptosis in malignant glioma cells both in vitro and in vivo", *Oncogene*, 26(17):2435-2444, 2007.
Kerr et al., "Of JAKs, STATs, blind watchmakers, jeeps and trains", *FEBS Lett.*, 546(1):1-5, 2003.
Meydan et al., "Inhibition of acute lymphoblastic leukaemia by a Jak-2 inhibitor", *Nature*, 379(6566):645-648, 1996.
Peng et al., "Tyrphostin-like compounds with ubiquitin modulatory activity as possible therapeutic agents for multiple myeloma", *Bioorg. Med. Chem.*, 19(23):7194-7204, 2011.
Peterson et al., "Targeting deubiquitinase activity with a novel small-molecule inhibitor as therapy for B-cell malignancies", *Blood*, 125(23):3588-3597, 2015.
Swiatek-Machado et al., "Novel small molecular inhibitors disrupt the JAK/STAT3 and FAK signaling pathways and exhibit a potent antitumor activity in glioma cells", *Cancer Biol. Ther.*, 13(8):657-670, 2012.
Verma et al., "Jak family of kinases in cancer", *Cancer Metastasis Rev.*, 22(4):423-434, 2003.
Yu and Jove, "The STATs of cancer—new molecular targets come of age", *Nature Rev. Cancer*, 4(2):97-105, 2004.

CAFFEIC ACID DERIVATIVES AND USES THEREOF

The present application claims the priority benefit of U.S. Provisional Patent Application No. 62/584,591, filed Nov. 10, 2017, the entire contents of which are incorporated herein by reference.

BACKGROUND

1. Field

The present invention relates generally to the treatment of cell proliferative diseases such as cancer. More particularly, it concerns caffeic acid derivatives useful for the treatment of cell proliferative diseases such as cancer, pharmaceutical compositions comprising these compounds, and methods of treatment employing these compounds or compositions.

2. Related Art

The compound AG490 is a kinase inhibitor that inhibits Janus kinase 2/Signal transducer and activator of transcription-3 (Jak2/STAT3) signaling pathway. AG490 belongs to a group of compounds defined by the parent natural product caffeic acid and its natural derivatives like caffeic acid benzyl ester.

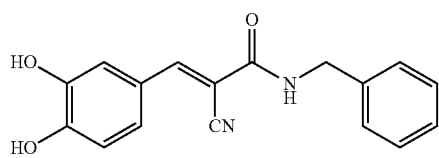

AG490

Targeted inhibition of the Jak2/STAT3 pathway with caffeic acid analogs such as AG490 inhibits tumor cell growth and increases sensitivity to apoptotic stimuli; thus, inhibitors of this pathway may be used as potential therapeutics for cancer therapy (Catlett-Falcone et al., 1999; Alas and Bonavida, 2003; Burdelya et al., 2002). AG490 suffers from potential instability in biological matrices (blood, tissues, etc) and relatively low potency (Kondo, et al., 2007; Burdelya et al., 2002; Meydan et al., 1996; Constantin et al., 1998). Receptor-based or direct activation of Jak2/STAT3 pathway by such stimulators such as EGF, scr, and IL-6 (multiple interleukins and cytokines) promoting survival proliferation and angiogenesis of human tumors (Bharti et al., 2003, Verma et al., 2003, Kerr et al., 2003), requires inhibitors more potent and more stable than AG490 to have potential as anti-cancer drugs.

Jak2/STAT3 signaling pathways participate in the progression of a variety of malignancies. STAT3 is constitutively activated in pancreatic carcinoma, glioblastoma multiforme, and squamous cell carcinoma of the head and neck, among others, and its activation has been shown to affect VEGF expression, angiogenesis, tumor growth, and metastasis in vivo. As such, STAT3 remains an excellent target for drug development (Yu and Jove, 2004).

AG490, a caffeic acid analog, is sometimes referred descriptively as a tyrphostin. U.S. Pat. Nos. 6,426,366, 7,745,468, 8,143,412 and 8,779,151 and U.S. Patent Publication No. 2003/0013748 describe derivates of AG490.

AG490, however, has limited activity in animal studies and must be used at high concentrations (~50 to 100 μM) to achieve inhibition of Jak2/STAT3 signaling and anti-tumor effects. This low potency of AG490 is insufficient to warrant clinical investigation of this compound for the treatment of cancer (Burdelya et al., 2002; Meydan et al., 1996; Constantin et al., 1998). And even in view of of further derivatives of AG490, such as WP1066, that have been developed in the interim, a need continues to exist for new therapeutics that exhibit strong anti-proliferative effects, at low therapeutic concentrations, and with favorable pharmacokinetic and toxicological properties.

SUMMARY

In some aspects, the present disclosure provides caffeic acid derivatives which may be used to treat or prevent diseases or disorders. In some embodiments, the compounds are further defined by the formula:

In some aspects, the present disclosure provides compounds of the formula:

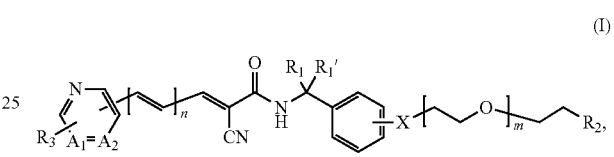

(I)

wherein:
  $A_1$ and $A_2$ are each independently —CH= or —N=, provided that $A_1$ and $A_2$ are not both —N=;
  m is 0-6;
  n is 0, 1, or 2;
  X is O, S, or $NR_4$;
    wherein $R_4$ is hydrogen, alkyl$_{(C1-6)}$, or substituted alkyl$_{(C1-6)}$;
  $R_1$ and $R_1'$ are each independently alkyl$_{(C1-8)}$, cycloalkyl$_{(C3-8)}$, -alkanediyl$_{(C1-C8)}$-cycloalkyl$_{(C3-8)}$, alkenyl$_{(C2-8)}$, alkynyl$_{(C2-8)}$, aryl$_{(C6-12)}$, aralkyl$_{(C7-12)}$, or a substituted version of any of these groups, or
  $R_1$ and $R_1'$ are taken together and are alkanediyl$_{(C2-8)}$ or substituted alkanediyl$_{(C2-8)}$;
  $R_2$ is heterocycloalkyl$_{(C2-12)}$, dialkylamino$_{(C2-8)}$, heteroaryl$_{(C1-8)}$, alkylamino$_{(C1-8)}$, arylamino$_{(C6-8)}$, alkoxy$_{(C1-8)}$, aryloxy$_{(C6-12)}$, or substituted versions of any of these groups; and
  $R_3$ is halo, hydrogen, hydroxy, amino, cyano or mercapto;
or a pharmaceutically acceptable salt thereof.

In some embodiments, the compound is further defined as:

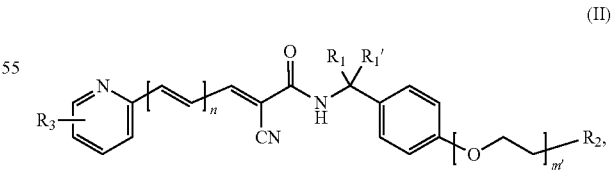

(II)

wherein:
  m' is 1-4;
  n is 0 or 1;
  $R_1$ and $R_1'$ are each independently alkyl$_{(C1-8)}$, cycloalkyl$_{(C3-8)}$, -alkanediyl$_{(C1-C8)}$-cycloalkyl$_{(C3-8)}$, alkenyl$_{(C2-8)}$, alkynyl$_{(C2-8)}$, aryl$_{(C6-12)}$, aralkyl$_{(C7-12)}$, or a substituted version of any of these groups;

R₂ is heterocycloalkyl$_{(C2-12)}$, dialkylamino$_{(C2-8)}$, heteroaryl$_{(C1-8)}$, alkylamino$_{(C1-8)}$, arylamino$_{(C6-8)}$, alkoxy$_{(C1-8)}$, aryloxy$_{(C6-12)}$, or substituted versions of any of these groups; and R₃ is halo, hydrogen, hydroxy, amino, cyano or mercapto; or a pharmaceutically acceptable salt thereof.

In some embodiments, the compound is further defined as:

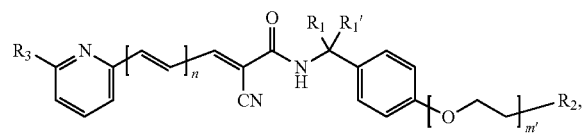

wherein:
m' is 1-4;
n is 0 or 1;
R₁ and R₁' are each independently alkyl$_{(C1-8)}$, cycloalkyl$_{(C3-8)}$, -alkanediyl$_{(C1-C8)}$-cycloalkyl$_{(C3-8)}$, alkenyl$_{(C2-8)}$, alkynyl$_{(C2-8)}$, aryl$_{(C6-12)}$, aralkyl$_{(C7-12)}$, or a substituted version of any of these groups;

R₂ is heterocycloalkyl$_{(C2-12)}$, dialkylamino$_{(C2-8)}$, heteroaryl$_{(C1-8)}$, alkylamino$_{(C1-8)}$, arylamino$_{(C6-8)}$, alkoxy$_{(C1-8)}$, aryloxy$_{(C6-12)}$, or substituted versions of any of these groups; and R₃ is halo, hydrogen, hydroxy, amino, cyano or mercapto; or a pharmaceutically acceptable salt thereof.

In some embodiments, m is 0-2. In some embodiments, m is 0 or 1. In some embodiments, m is 0. In other embodiments, m is 1. In yet other embodiments, m is 2. In some embodiments, m' is 1-3. In some embodiments, m' is 1 or 2. In some embodiments, m' is 1. In other embodiments, m' is 2. In yet other embodiments, m' is 3. In some embodiments, n is 0. In some embodiments, n is 1. In some embodiments, R₁ is alkyl$_{(C1-8)}$ such as ethyl or propyl. In some embodiments, R₁' is alkyl$_{(C1-8)}$ such as ethyl or propyl. In some embodiments, R₂ is heterocycloalkyl$_{(C2-12)}$. In some embodiments, R₂ is heterocycloalkyl$_{(C2-8)}$. In some embodiments, R₂ is N-heterocycloalkyl$_{(C2-8)}$ such as morpholinyl or 4-methylpiperazin-1-yl. In other embodiments, R₂ is dialkylamino$_{(C2-8)}$ such as diethylamino. In some embodiments, R₃ is halo such as chloro or bromo. In other embodiments, R₃ is hydrogen. In some embodiments, the compound is in the form of a pharmaceutically acceptable salt such as an HCl salt or a maleic acid salt. In other embodiments, the compound is not in the form of a salt.

In some embodiments, the compound is further defined as:

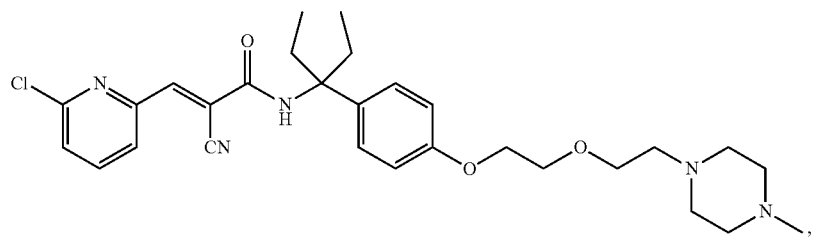

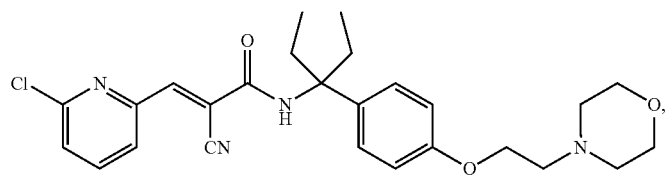

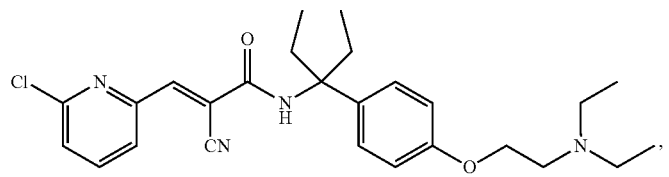

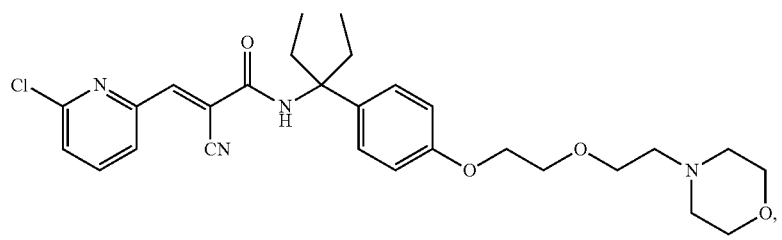

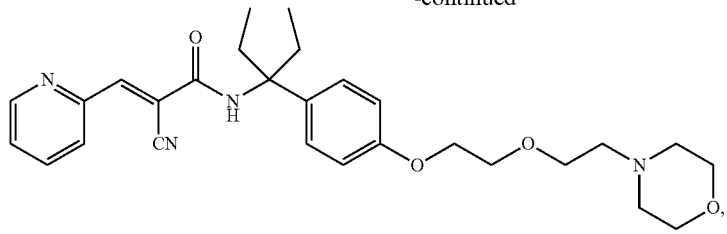
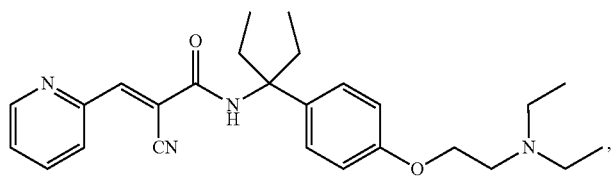
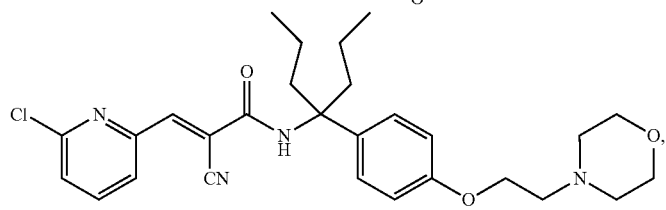
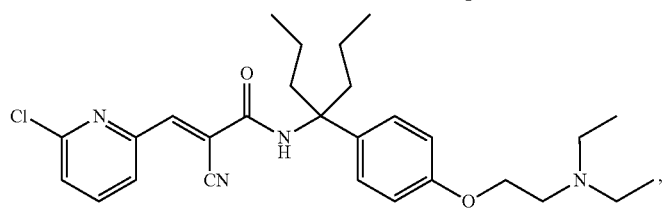
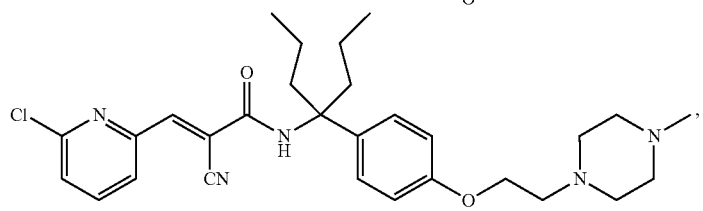
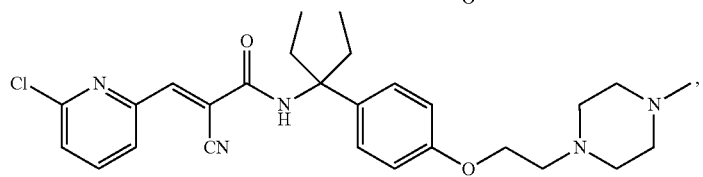
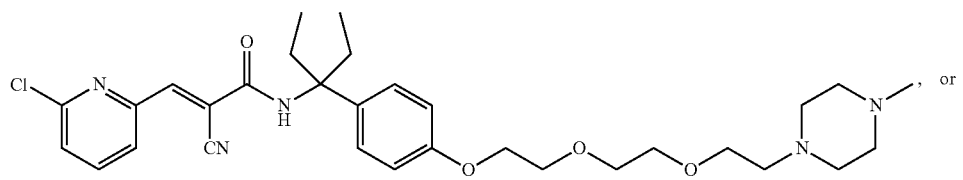
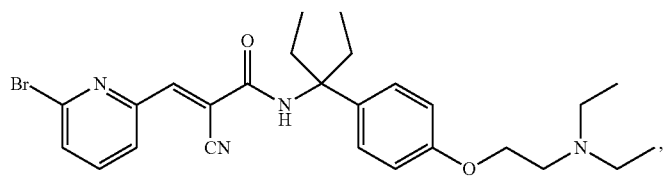
or a pharmaceutically acceptable salt of any of these formulas. In some embodiments, the pharmaceutically acceptable salt comprises HCl or maleic acid.

In some embodiments, the compound is further defined as:

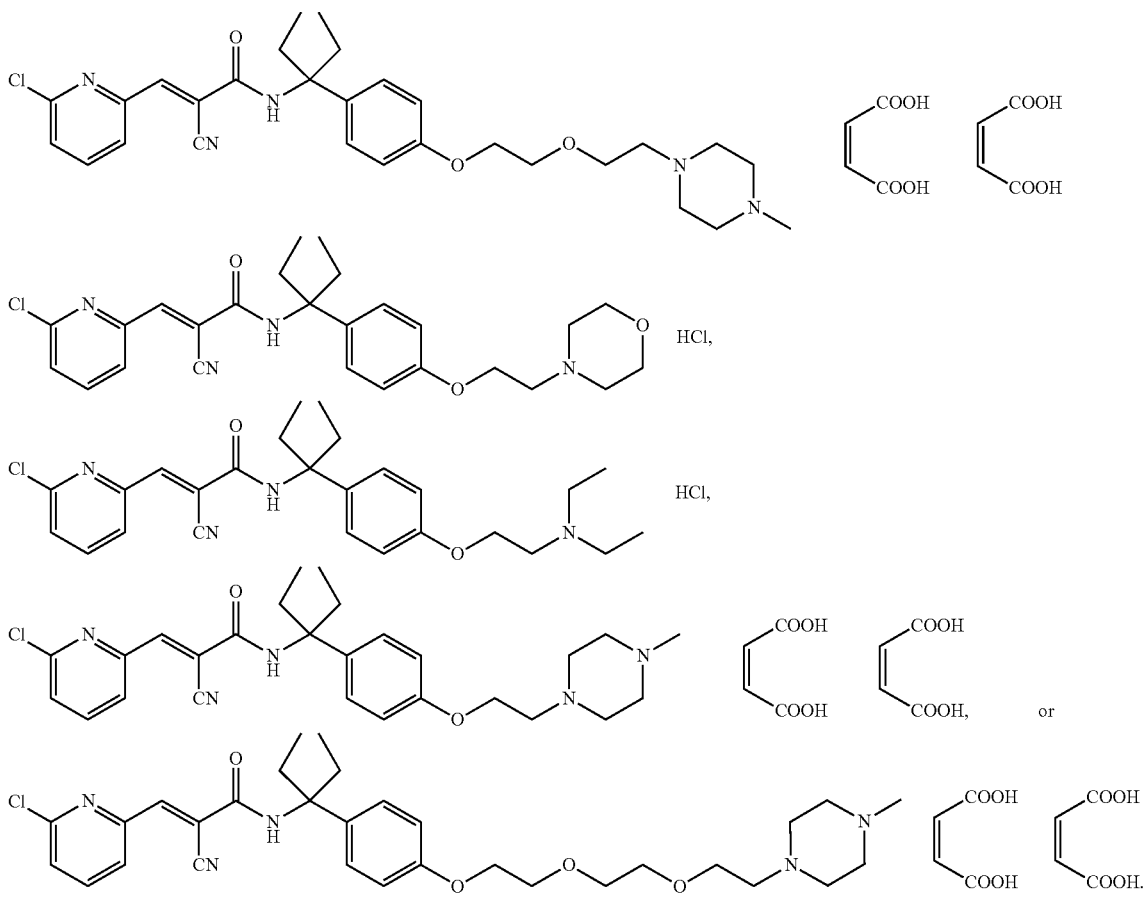

In some aspects, the present disclosure provides pharmaceutical compositions comprising:
a) a compound disclosed herein; and
b) an excipient.

In some aspects, the present disclosure provides methods of treating and/or preventing a disease or a disorder in a patient in need thereof, comprising administering to the patient a compound or a pharmaceutical composition disclosed herein in an amount sufficient to treat and/or prevent the disease or disorder. In some embodiments, the disease or disorder is a hyperproliferative disease. In some embodiments, the hyperproliferative disease is a skin disease such as psoriasis. In other embodiments, the hyperproliferative disease is cancer. In some embodiments, the cancer is a carcinoma, sarcoma, lymphoma, leukemia, melanoma, mesothelioma, multiple myeloma, or seminoma. In some embodiments, the cancer is a cutaneous T-cell lymphoma (CTCL). In other embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the compound or pharmaceutical composition is administered orally, intraarterially, intravenously, or topically. In some embodiments, the compound or pharmaceutical composition is administered topically.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

The present disclosure provides caffeic acid derivatives. Also, provided herein are pharmaceutical compositions thereof and methods of using these compounds and their pharmaceutical compositions.

I. COMPOUNDS AND SYNTHETIC METHODS

The compounds of the present invention (also referred to as "compounds of the present disclosure") are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch of continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All of the compounds of the present invention may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. PHARMACEUTICAL FORMULATIONS AND ROUTES OF ADMINISTRATION

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound of the present invention formulated with one or more excipients and/or drug carriers appropriate to the indicated route of administration. In some embodiments, the compounds of the present invention are formulated in a manner amenable for the treatment of human and/or veterinary patients. In some embodiments, formulation comprises admixing or combining one or more of the compounds of the present invention with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g. subcutaneous, intravenous, intraperitoneal, etc.). Depending on the route of administration, the compounds of the present invention may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds of the present invention may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (including, but not limited to, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, including, but not limited to, parabens, chlorobutanol, phenol, ascorbic acid, and thimerosal. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds of the present invention can be administered orally, for example, with an inert diluent or an assimilable edible carrier. The compounds and other ingredients may also be enclosed in a hard or soft shell gelatin capsule, compressed into tablets, or incorporated directly into the subject's diet. For oral therapeutic administration, the compounds of the present invention may be incorporated with excipients and used in the form of ingestible tablets, buccal tablets, troches, capsules, elixirs, suspensions, syrups, wafers, and similar oral formulations. The percentage of the therapeutic compound in the compositions and preparations may, of course, be varied. The amount of the therapeutic compound in such pharmaceutical formulations is such that a suitable dosage will be obtained.

In some embodiments, the therapeutic compound may also be administered topically to the skin, eye, or mucosa. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3): 659-661, 2008, which is incorporated herein by reference):

$$\text{HED(mg/kg)}=\text{Animal dose(mg/kg)}\times(\text{Animal}K_m/\text{Human}K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, subjects may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

III. TREATMENT OF CANCER AND OTHER HYPERPROLIFERATIVE DISEASES

While hyperproliferative diseases can be associated with any disease which causes a cell to begin to reproduce uncontrollably, the prototypical example is cancer. Psoriasis is another example. One of the key elements of cancer is that the cell's normal apoptotic cycle is interrupted and thus agents that interrupt the growth of the cells are important as therapeutic agents for treating these diseases. In some embodiments, the caffeic acid derivatives described herein may be used to decreased cell counts and as such may be used to treat a variety of cancers or other malignancies.

In some embodiments, cancer, cancer tissue, or cancer cells may be treated by the compounds, methods, and compositions disclosed herein. In some embodimantes, cancer cells or tissue that may be treated include but are not limited to cells or tissue from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In some embodiments, the cancer that may be treated may be of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonenc apsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia, including hairy cell leukemia; chronic lymphocytic leukemia (CLL); acute lymphoblastic leukemia (ALL); acute myeloid leukemia (AML); and chronic myeloblastic leukemia.

In another aspect, the compounds, compositions, and methods disclosed herein may be used to treat cancer or other hyperproliferative diseases. While hyperproliferative diseases can be associated with any disease which causes a cell to begin to reproduce uncontrollably, the prototypical example is cancer. One of the elements of cancer is that the cell's normal apoptotic cycle is interrupted. As such, agents that interrupt the growth of the cells are important as therapeutic agents for treating these diseases. In this disclosure, the compounds of the present disclosure thereof may be used to lead to decreased cell counts and may be used to treat a variety of types of cancer.

In some embodiments, cancer cells that may be treated with the compounds or compositions of the present disclosure include, but are not limited to, bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, and uterus cells.

In some embodiments, tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

In certain embodiments regarding methods of treating cancer in a patient, comprising administering to the patient a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell.

The tumor cell may be any type of tumor cell, such as a brain cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, treatment methods further comprise monitoring treatment progress. In some of these embodiments, the method includes the step of determining a level of changes in hematological parameters and/or cancer stem cell (CSC) analysis with cell surface proteins as diagnostic markers or diagnostic measurement (e.g., screen, assay) in a patient suffering from or susceptible to a disorder or symptoms thereof associated with cancer in which the patient has been administered a therapeutic amount of a compound or composition as described herein. The level of the marker determined in the method can be compared to known levels of marker in either healthy normal controls or in other afflicted patients to establish the patient's disease status. In some embodiments, a second level of the marker in the patient is determined at a time point later than the determination of the first level, and the two levels are compared to monitor the course of disease or the efficacy of the therapy. In some embodiments, a pre-treatment level of marker in the patient is determined prior to beginning treatment according to the methods described herein; this pre-treatment level of marker can then be compared to the level of marker in the patient after the treatment commences, to determine the efficacy of the treatment.

In some embodiments, the patient is a mammal, e.g., a primate, preferably a higher primate, e.g., a human (e.g., a patient having, or at risk of having, a disorder described herein). In some embodiments, the patient is in need of enhancing the patient's immune response. In certain embodiments, the patient is, or is at risk of being, immunocompromised. For example, in some embodiments, the patient is undergoing or has undergone a chemotherapeutic treatment and/or radiation therapy. Alternatively, or in combination, the patient is, or is at risk of being, immunocompromised as a result of an infection.

IV. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

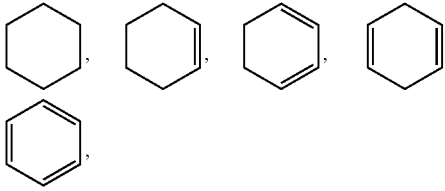 and

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ~~~ ", when drawn perpendicularly across a bond

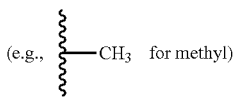 (e.g., —CH₃ for methyl)

indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀⦀" means a single bond where the group attached to the thick end of the wedge is "into the page". The symbol " ~~~ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

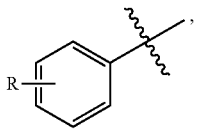

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

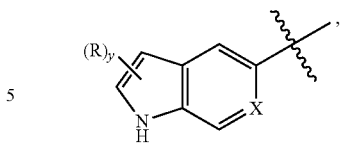

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

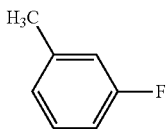

is also taken to refer to

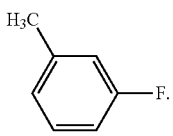

Aromatic compounds may also be depicted using a circle to represent the delocalized nature of the electrons in the fully conjugated cyclic π system, two non-limiting examples of which are shown below:

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

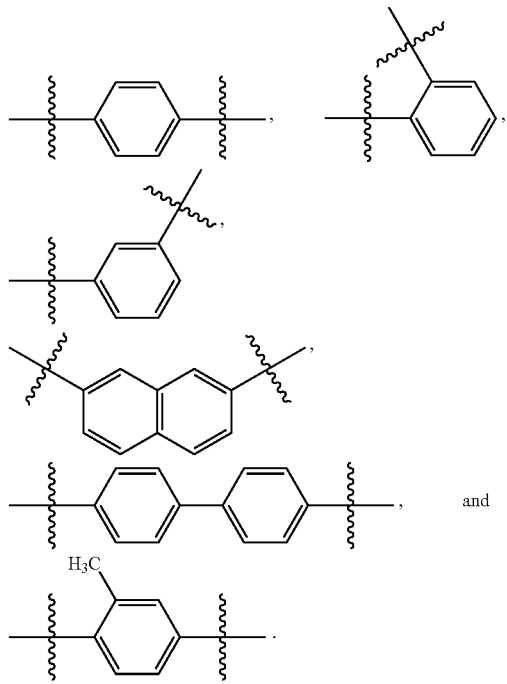

and

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O) CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O) CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$ OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH (CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH$_3$, —S(O)$_2$OH, or —S(O)$_2$NH$_2$. The groups, —C(O) CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC (CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$ OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$) (CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Design and Synthesis of Caffeic Acid Derivatives

TABLE 1

Structures of caffeic acid derivatives.

| Compound Identifier | Chemical Formula |
|---|---|
| WP1721 | |
| WP1722 | |
| WP1723 | |
| WP1724 | |
| WP1727 | |
| WP1730 | |
| WP1731 | |

TABLE 1-continued

Structures of caffeic acid derivatives.

| Compound Identifier | Chemical Formula |
|---|---|
| WP1732 | |
| WP1733 | |
| WP1734 | |
| WP1735 | |
| WP1793 | |
| WP1794 | |
| WP1795 | |

TABLE 1-continued

Structures of caffeic acid derivatives.

| Compound Identifier | Chemical Formula |
|---|---|
| WP1796 | |
| WP1797 | |
| WP1798 | |

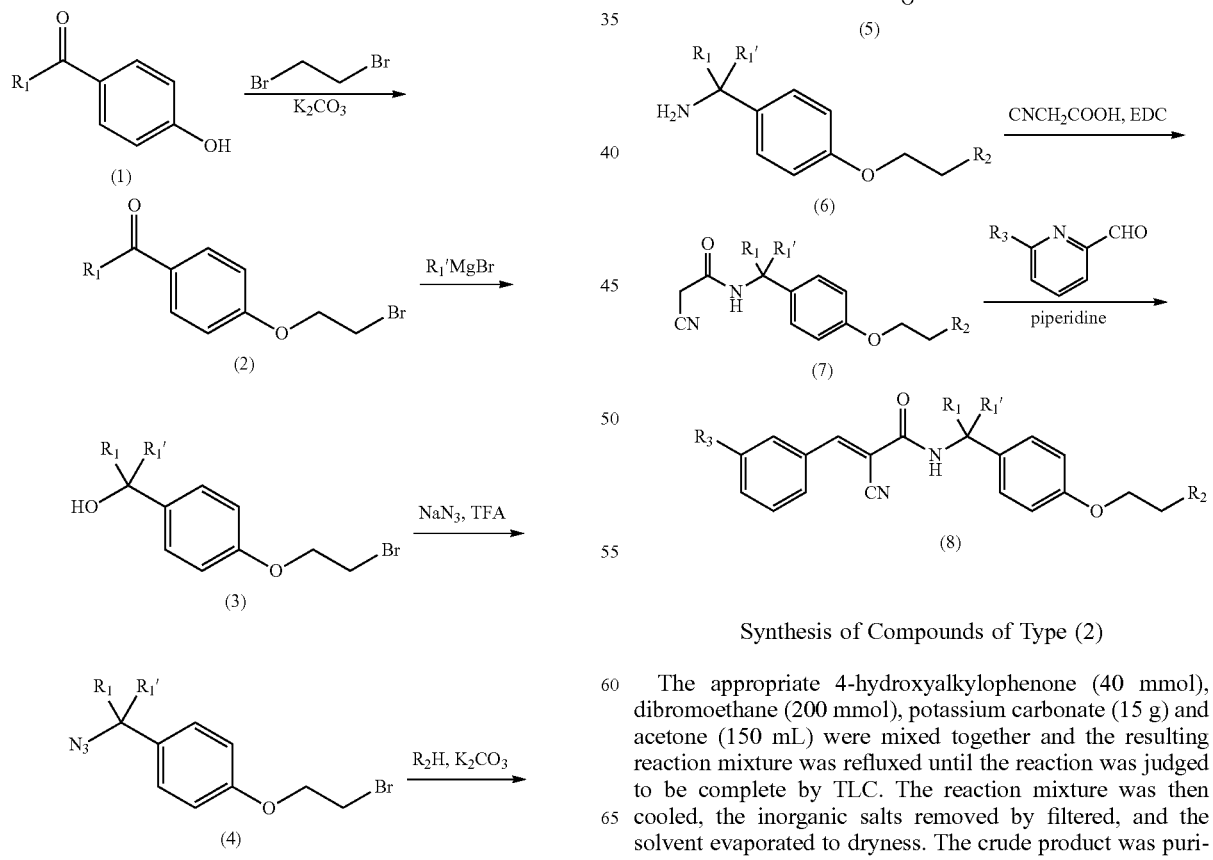

Scheme 1. General synthetic route employed in the synthesis of caffeic acid derivatives of type 8. Compounds WP1721, WP1722, WP1730, WP1733, WP1734 and WP1735 were obtained according to the method shown in Scheme 1.

Synthesis of Compounds of Type (2)

The appropriate 4-hydroxyalkylophenone (40 mmol), dibromoethane (200 mmol), potassium carbonate (15 g) and acetone (150 mL) were mixed together and the resulting reaction mixture was refluxed until the reaction was judged to be complete by TLC. The reaction mixture was then cooled, the inorganic salts removed by filtered, and the solvent evaporated to dryness. The crude product was purified by LC using a toluene/ethyl acetate gradient. Fractions containing product were pooled together and evaporated to dryness. The following compounds were prepared according to this procedure:

1-(4-(2-bromoethoxy)phenyl)propan-1-one (2a, $R_1=R_1'=Et$)

Yield 85%, $^1H$ NMR (CDCl$_3$, 300 MHz, δ) ppm, 7.98-7.93 (m, 2H), 6.97-6.92 (m, 2H), 4.35 (dd, 2H, J=6.1 Hz, J=6.3 Hz), 3.66 (dd, 1H, J=6.3 Hz, J=6.2 Hz), 2.95 (q, 2H, J=7.2 Hz), 1.22 (t, 3H, J=7.2 Hz)

1-(4-(2-bromoethoxy)phenyl)butan-1-one (2b, $R_1=R_1'=Pr$)

Yield 83%, $^1H$ NMR (CDCl$_3$, 300 MHz, δ) ppm, 7.98-7.92 (m, 2H), 6.97-6.91 (m, 2H), 4.35 (dd, 2H, J=6.1 Hz, J=6.2 Hz), 3.66 (dd, 1H, J=6.2 Hz, J=6.3 Hz), 1.83-1.69 (m, 2H), 1.0 (t, 3H, J=7.2 Hz, J=7.4 Hz)

Synthesis of Compounds of Type (3)

The appropriate alkylmagnesium bromide (14 mmol) was added dropwise to the vigorously stirred solution of the appropriate 1-(4-(2-bromoethoxy)phenyl)alkyl-1-one (12 mmol) in THF (90 mL). The resultant reaction mixture was stirred at room temperature for 1 h and the progress of the reaction was monitored by TLC. After the reaction was judge to be complete, the reaction mixture was poured into ice-cold 1 N HCl solution (60 ml). After 20 min of stirring, the product was extracted with ethyl acetate. The organic extract was washed with a 10% solution of sodium bicarbonate, then with brine, and the resulting solution was dried over anhydrous Na$_2$SO$_4$. The drying agent and solvents were removed and the product was purified by LC using toluene/ethyl acetate gradient for elution. Fractions containing product were pooled together and evaporated to dryness. The following compounds were prepared according to this procedure:

3-(4-(2-bromoethoxy)phenyl)pentan-3-ol (3a, $R_1=R_1'=Et$)

Yield 72%, $^1H$ NMR (CDCl$_3$, 300 MHz, δ) ppm, 7.32-7.27 (m, 2H), 6.91-6.85 (m, 2H), 4.29 (dd, 2H, J=6.4 Hz, J=6.3 Hz), 3.64 (dd, 2H, J=6.3 Hz, J=6.3 Hz), 1.90-1.71 (m, 4H), 0.75 (t, 6H, J=7.4 Hz)

4-(4-(2-bromoethoxy)phenyl)heptan-4-ol (3b, $R_1=R_1'=Pr$)

Yield 65%, $^1H$ NMR (CDCl$_3$, 300 MHz, δ) ppm; 7.33-7.24 (m, 2H), 6.91-6.83 (m, 2H), 4.22 (dd, 2H, J=6.3 Hz, J=6.3 Hz), 3.63 (dd, 2H, J=6.3 Hz, J=6.3 Hz), 1.85-1.66 (m, 4H), 1.40-1.18 (m, 2H), 1.153-0.97 (m, 2H), 0.85 (t, 6H, J=7.2 Hz)

Synthesis of Compounds of Type (4)

A mixture of compound (3) (6 mmol), NaN$_3$ (24 mmol), and chloroform (20 mL) was prepared and vigorously stirred and cooled to 0° C. Trifluoroacetic acid (40 mmol) was added and the reaction mixture was stirred at 0° C. After reaction was judged to be complete by TLC, the mixture was diluted with chloroform (30 mL) and then water (30 mL) was added. The organic and aqueous layers were separated. The organic layer was washed with water and subsequently dried over anhydrous sodium sulfate. The product was purified by column chromatography using a hexanes/ethyl acetate gradient for elution. Fractions containing product were pooled together and evaporated to dryness. The following compounds were prepared according to this procedure:

1-(3-azidopentan-3-yl)-4-(2-bromoethoxy)benzene (4a, $R_1=R_1'=Et$)

Yield 85.6%, $^1H$ NMR (CDCl$_3$, 300 MHz, δ) ppm, 7.29-7.21 (m, 2H), 6.94-6.85 (m, 2H), 4.29 (dd, 2H, J=6.3 Hz, J=6.3 Hz), 3.64 (dd, 2H, J=6.3 Hz, J=6.3 Hz), 2.05-1.82 (m, 4H), 0.78 (t. 6H, J=7.4 Hz)

1-(4-azldoheptan-4-yl)-4-(2-bromoethoxy)benzene (4b, $R_1=R_1'=Pr$)

Yield 84.8%, $^1H$ NMR (CDC$_3$, 300 MHz, δ) ppm; 7.28-7.21 (m, 2H), 6.91-6.84 (m, 2H), 4.28 (dd, 2H, J=6.3 Hz, J=6.3 Hz), 3.63 (dd, 2H, J=6.3 Hz, J=6.3 Hz), 1.96-1.75 (m, 4H), 1.40-1.18 (m, 2H), 1.40-1.16 (m, 2H), 1.16-1.00 (m, 2H), 0.88 (t, 6H, J=7.2 Hz)

Synthesis of Compounds of Type (5)

A mixture of the appropriate compound (4) (2 mmol), amine (2.2 mmol), potassium carbonate (20 mmol), and acetonitrile (10 mL) was prepared and the mixture was refluxed with vigorous stirring. Reaction progress was monitored by TLC. After the reaction was judged to be complete, the reaction mixture was cooled and then diluted with chloroform. The inorganic salts were removed by filteration, the solvents were evaporated, and the crude product was purified by LC using a chloroform/methanol gradient for elution. Fractions containing product were pooled together and evaporated to dryness. The following compounds were prepared according to this procedure:

4-(2-(4-(3-azidopentan-3-yl)phenoxy)ethyl)morpholine (5a, $R_1=R_1'=Et$, $R_2$=morpholinyl)

Yield 80%. $^1H$ NMR (CDCl$_3$, 300 MHz, δ) ppm; 7.25-7.20 (m, 2H), 6.92-6.85 (m, 2H), 4.11 (dd, 2H, J=5.7 Hz, J=5.7 Hz), 3.74 (dd, 2H, J=4.4 Hz, J=4.6 Hz), 2.81 (dd, 2H, J=5.7 Hz, J=5.7 Hz), 2.58 (dd, 2H, J=4.7 Hz, J=4.6 Hz), 2.03-1.82 (m, 4H), 0.78 (t. 6H, J=7.4 Hz)

2-(4-(3-azidopentan-3-yl)phenoxy)-N,N-diethylethan-1-amine (5b, $R_1=R_1'=Et$, $R_2$=diethylamine)

Yield 95%. $^1H$ NMR (CDCl$_3$, 300 MHz, δ) ppm; 7.25-7.18 (m, 2H), 6.92-6.83 (m, 2H), 4.04 (dd, 2H, J=6.3 Hz, J=6.3 Hz), 2.89 (dd, 2H, J=6.3 Hz, J=6.3 Hz), 2.65 (q, 4H, J=7.1 Hz), 2.14-1.80 (m, 4H), 1.80 (t, 6H, J=7.1 Hz), 0.78 (t, 6H, J=7.4 Hz)

4-(2-(4-(4-azidoheptan-4-yl)phenoxy)ethyl)morpholine (5c, $R_1=R_1'=Pr$, $R_2$=morpholinyl)

Yield 95.3%. $^1H$ NMR (CDCl$_3$, 300 MHz, δ) ppm; 7.25-7.20 (m, 2H), 6.92-6.83 (m, 2H), 4.10 (dd, 2H, J=5.7 Hz, J=5.7 Hz), 3.73 (dd, 2H, J=4.6 Hz, J=4.7 Hz), 2.80 (dd, 2H, J=5.7 Hz, J=5.7 Hz), 2.58 (dd, 2H, J=4.7 Hz, J=4.7 Hz), 1.95-1.74 (m, 4H), 1.38-1.00 (m, 4H), 0.86 (t, 6H, J=7.3 Hz)

1-(2-(4-(4-azidoheptan-4-yl)phenoxy)ethyl)-4-methylpiperazine (5d, $R_1=R_1'=Pr$, $R_2$=4-methyl-piperazinyl)

Yield 78.3%. $^1$H NMR (CDCl$_3$, 300 MHz, δ) ppm; 7.25-7.18 (m, 2H), 6.90-6.83 (m, 2H), 4.10 (dd, 2H, J=5.9 Hz, J=5.9 Hz), 2.81 (dd, 2H, J=5.9 Hz, J=5.9 Hz), 2.70-2.36 (m, 8H), 2.39 (s, 3H), 1.96-1.75 (m, 4H), 1.38-1.00 (m, 4H), 0.86 (t, 6H, J=7.3 Hz)

Synthesis of Compounds of Type (6)

The appropriate compound (5) (1 g) was dissolved in the mixture of THF/EtOH (1:1 v/v) (15 ml). Pd/C (10% wet Degussa type, 100 mg) was added and the reaction mixture was exposed to hydrogen gas using a Paar apparatus (40 p.s.i.) overnight. After the reaction was completed the reaction mixture was filtered trough Celite, solvent was evaporated and product was purified by LC system using chloroform/methanol gradient as eluent. Fractions containing product were pooled together and evaporated to dryness. The following compounds were prepared according to this procedure:

3-(4-(2-(diethylamino)ethoxy)phenyl)pentan-3-amine (6a, $R_1=R_1'$=Et, $R_2$=diethylamine)

Yield ~100%. $^1$H NMR (CDCl$_3$, 300 MHz, δ) ppm; 7.32-7.25 (m, 2H), 6.89-6.83 (m, 2H), 4.04 (dd, 2H, J=6.5 Hz, J=6.4 Hz), 2.89 (dd, 2H, J=6.4 Hz, J=6.4 Hz), 2.65 (q, 4H, J=7.1 Hz), 1.87-1.73 (m, 2H), 1.72-1.55 (m, 2H), 1.07 (t, 6H, J=7.1 Hz), 0.72 (t, 6H, J=7.4 Hz)

4-(4-(2-morpholinoethoxy)phenyl)heptan-4-amine (6b, $R_1=R_1'$=Pr, $R_2$=morpholinyl)

Yield 75.4%. $^1$H NMR (CDC$_3$, 300 MHz, δ) ppm; 7.32-7.26 (m, 2H), 6.88-6.83 (m, 2H), 4.10 (dd, 2H, J=5.7 Hz, J=5.7 Hz), 3.73 (dd, 2H, J=4.5 Hz, J=4.8 Hz), 2.80 (dd, 2H, J=5.7 Hz, J=5.7 Hz), 2.58 (dd, 2H, J=4.7 Hz, J=4.7 Hz), 1.85-1.58 (m, 2H), 1.30-1.00 (m, 2H), 0.84 (t. 6H, J=7.2 Hz)

4-(4-(2-(diethylamino)ethoxy)phenyl)heptan-4-amine (6c, $R_1=R_1'$=Pr, $R_2$=diethylamino)

Yield 73.8%. $^1$H NMR (CDCl$_3$, 300 MHz, δ) ppm; 7.32-7.26 (m, 2H), 6.88-6.81 (m, 2H), 4.04 (dd, 2H, J=6.4 Hz, J=6.4 Hz), 2.87 (dd, 2H, J=6.4 Hz, J=6.4 Hz), 2.64 (q, 4H, J=7.1 Hz), 1.80-1.54 (m, 8H), 1.30-1.12 (m, 2H), 1.12-0.90 (m, 2H), 1.07 (t, 3H, J=7.1 Hz), 0.83 (t, 3H, J=7.1 Hz)

4-(4-(2-(4-methylpiperazin-1-yl)ethoxy)phenyl)heptan-4-amine (6d, $R_1=R_1'$=Pr, $R_2$=4-methyl-piperazinyl)

Yield 65.7%. $^1$H NMR (DMSO-d$_6$, 300 MHz, δ) ppm; 8.52 (bs, 2H), 7.40-7.30 (m, 2H), 7.72-6.95 (m, 2H), 4.20-4.0 (m, 2H), 3.50-3.30 (m, 2H), 3.33 (s, 3H), 3.20-2.55 (m, 8H), 2.00-1.72 (m, 2H), 1.28-1.00 (m, 2H), 1.07 (t, 3H, J=7.0 Hz), 0.83 (t, 3H, J=7.3 Hz)

Synthesis of Compounds of Type (7)

EDC (2.0 mmol) followed by DMAP (0.01 mmol) were added to the solution of the appropriate compound (6) (1 mmol) and cyanoacetic acid (2.5 mmol) in DCM (10 mL) and the resulting mixture was stirred at room temperature overnight. The crude product was purified by LC using a chloroform/methanol gradient as eluent. Fractions containing product were pooled together and evaporated to dryness. The following compounds were prepared according to this procedure:

2-cyano-N-(3-(4-(2-morpholinoethoxy)phenyl)pentan-3-yl)acetamide (7a, $R_1=R_1'$=Et, $R_2$=morpholino)

Yield 60%. $^1$H NMR (CDCl$_3$, 300 MHz, δ) ppm; 7.25-7.17 (m, 2H), 6.92-6.85 (m, 2H), 6.14 (bs, 1H, 4.10 (dd, 2H, J=5.7 Hz, J=5.7 Hz), 3.73 (dd, 2H, J=4.6 Hz, J=4.8 Hz), 3.34 (s, 2H), 2.79 (dd, 2H, J=5.6 Hz, J=5.8 Hz), 2.58 (dd, 2H, J=4.7 Hz, J=4.6 Hz), 2.22-1.95 (m, 2H), 0.75 (t, 6H, J 7.4 Hz)

2-cyano-N-(3-(4-(2-(diethylamino)ethoxy)phenyl) pentan-3-yl)acetamide (7b, $R_1=R_1'$=Et, $R_2$=diethylamino)

Yield 70.4%. $^1$H NMR (CDCl$_3$, 300 MHz, δ) ppm; 7.25-7.17 (m, 2H), 6.92-6.85 (m, 2H), 6.15 (bs, 1H, 4.03 (dd, 2H, J=6.4 Hz, J=6.4 Hz), 3.37 (s, 2H), 2.87 (dd, 2H, J=6.4 Hz, J=6.4 Hz), 2.65 (q, 2H, J=7.1 Hz), 2.22-2.00 (m, 2H), 1.07 (t, 6H, J=7.1 Hz), 0.74 (t, 6H, J=7.4 Hz)

2-cyano-N-(4-(4-(2-(diethylamino)ethoxy)phenyl) heptan-4-yl)acetamide (7c, $R_1=R_1'$=Pr, $R_2$=diethylamino)

Yield 60.4%. $^1$H NMR (CDCl$_3$, 300 MHz, δ) ppm; 7.25-7.17 (m, 2H), 6.92-6.85 (m, 2H), 6.18 (bs, 1H, 4.04 (dd, 2H, J=6.4 Hz, J=6.4 Hz), 3.33 (s, 2H), 2.90 (dd, 2H, J=6.3 Hz, J=6.3 Hz), 2.68 (q, 2H, J=7.1 Hz), 2.22-1.98 (m, 4H), 1.22-1.08 (m, 4H), 1.08 (t, 6H, J=7.1 Hz), 0.87 (t, 6H, J=7.3 Hz)

2-cyano-N-(4-(4-(2-morpholinoethoxy)phenyl)heptan-4-yl)acetamide (7d, $R_1=R_1'$=Pr, $R_2$=morpholinyl)

Yield 93.4%. $^1$H NMR (CDCl$_3$, 300 MHz, δ) ppm; 7.25-7.17 (m, 2H), 6.92-6.85 (m, 2H), 6.14 (bs, 1H, 4.10 (dd, 2H), J=5.7 Hz, J=5.7 Hz), 3.73 (dd, 2H, J=4.7 Hz, J=4.7 Hz), 3.33 (s, 2H), 2.80 (dd, 2H, J=5.7 Hz, J=5.7 Hz), 2.58 (dd, 4H, J=4.7 Hz, J=4.7 Hz), 2.19-1.90 (m, 4H), 1.22-1.03 (m, 4H), 0.88 (t, 6H, J=7.1 Hz)

2-cyano-N-(4-(4-(2-(4-methylpiperazin-1-yl)ethoxy) phenyl)heptan-4-yl)acetamide (7e, $R_1=R_1'$=Pr, $R_2$=4-methylpiperazinyl)

Yield 65.5%. $^1$H NMR (CDCl$_3$, 300 MHz, δ) ppm; 7.25-7.17 (m, 2H), 6.88-6.85 (m, 2H), 6.21 (bs, 1H), 4.10 (dd, 2H, J=5.7 Hz, J=5.7 Hz), 3.49 (s, 2H), 3.29 (s, 3H), 3.13 (dd, 8H, J=5.7 Hz), 2.91 (dd 2H, J=5.0 Hz, J=5.1 Hz), 2.19-1.90 (m, 4H), 1.22-1.03 (m, 4H), 0.88 (t, 6H, J=7.1 Hz)

Synthesis of Compounds of Type (8)

A mixture of the appropriate compound (7) (1 mmol), the appropriate 6-substituted picolinaldehyde (1.2 mmol), piperidine (0.1 mmol), and acetonitrile (20 mL) was prepared and refluxed with stirring. The progress of the reaction was monitored by TLC. After reaction was judged to be complete, the reaction mixture was evaporated to dryness and the crude product was purified by LC using a chloroform/methanol gradient as eluent. Fractions containing product were pooled together and evaporated to dryness. The following compounds were prepared according to this procedure:

(E)-3-(6-chloropyridin-2-yl)-2-cyano-N-(3-(4-(2-morpholinoethoxy)phenyl)pentan-3-yl)acrylamide (WP1721)

Yield 86.3%. $^1$H NMR (CDCl$_3$, 300 MHz, δ) ppm; 8.13 (s, 1H), 7.76 (dd, 1H, J=J=7.7 Hz), 7.48 (d, 1H, J=7.1 Hz), 7.42 (dd, 1H, J=8.0 Hz, J=0.6 Hz), 7.30-7.20 (m, 2H), 6.92-6.85 (m, 2H), 6.71 (bs, 1H), 4.10 (dd, 2H, J=5.7 Hz, J=5.7 Hz), 3.73 (dd, 2H, J=4.6 Hz, J=4.7 Hz), 2.79 (dd, 2H, J=5.7 Hz, J=5.7 Hz), 2.57 (dd, 4H, J=4.7 Hz, J=4.7 Hz), 2.30-2.23 (m, 4H), 0.78 (t, 6H, J=7.3 Hz)

(E)-3-(6-chloropyridin-2-yl)-2-cyano-N-(3-(4-(2-(diethylamino)ethoxy)phenyl)pentan-3-yl)acrylamide (WP1722)

Yield 84.2%. $^1$H NMR (CDCl$_3$, 300 MHz, δ) ppm; 8.14 (s, 1H), 7.76 (dd, 1H, J=J=7.7 Hz), 7.49 (d, 1H, J=7.2 Hz), 7.42 (dd, 1H, J=8.0 Hz, J=0.8 Hz), 7.30-7.20 (m, 2H), 6.92-6.86 (m, 2H), 6.71 (bs, 1H), 4.03 (dd, 2H, J=6.4 Hz, J=6.4 Hz), 2.88 (dd, 2H, J=6.4 Hz, J=6.4 Hz), 2.63 (q, 4H, J=7.1 Hz), 2.29-2.04 (m, 4H), 1.05 (t, 6H, J=7.1 Hz), 0.77 (t, 6H, J=7.3 Hz)

(E)-2-cyano-N-(3-(4-(2-(diethylamino)ethoxy)phenyl)pentan-3-yl)-3-(pyridin-2-yl)acrylamide (WP1727)

Yield 65.3%. $^1$H NMR (CDCl$_3$, 300 MHz, δ) ppm; 8.82 (dd, 1H, J=4.7 Hz, J=0.8 Hz), 8.21 (s, 1H), 7.80 (ddd, 1H, J=J=7.7 Hz, J=1.8 Hz), 7.55 (d, 1H, J=7.8 Hz), 7.39 (ddd, 1H, J=7.7 Hz, J=4.7 Hz, J=1.0 Hz), 7.30-7.22 (m, 2H), 6.93-6.85 (m, 2H), 6.72 (bs, 1H), 4.03 (dd, 2H, J=6.4 Hz, J=6.4 Hz), 2.86 (dd, 2H, J=6.4 Hz, J=6.4 Hz), 2.63 (q, 4H, J=7.2 Hz), 2.28-2.21 (m, 4H), 1.06 (t, 6H, J=7.2 Hz), 0.78 (t, 6H, J=7.3 Hz)

(E)-3-(6-chloropyridin-2-yl)-2-cyano-N-(4-(4-(2-morpholinoethoxy)phenyl)heptan-4-yl)acrylamide (WP1733)

Yield 83.7%. $^1$H NMR (CDCl$_3$, 300 MHz, δ) ppm; 8.13 (s, 1H), 7.76 (dd, 1H, J=J=7.8 Hz), 7.49 (d, 1H, J=7.2 Hz), 7.42 (d, 1H, J=8.0 Hz), 7.29-7.22 (m, 2H), 6.92-6.86 (m, 2H), 6.73 (bs, 1H), 4.10 (dd, 2H, J=6.7 Hz, J=6.7 Hz), 3.73 (dd, 2H, J=4.7 Hz, J=4.7 Hz), 2.79 (dd, 2H, J=4.7 Hz, J=4.7 Hz), 2.58 (dd, 4H, J=4.6 Hz, J=4.7 Hz), 2.22-1.97 (m, 4H), 0.89 (t, 6H, J=7.1 Hz)

(E)-3-(6-chloropyridin-2-yl)-2-cyano-N-(4-(4-(2-(diethylamino)ethoxy)phenyl)heptan-4-yl)acrylamide (WP1734)

Yield 74%. $^1$H NMR (CDCl$_3$, 300 MHz, δ) ppm; 8.14 (s, 1H), 7.76 (dd, 1H, J=J=7.7 Hz), 7.49 (d, 1H, J=7.2 Hz), 7.42 (d, 1H, J=8.0 Hz), 7.28-7.21 (m, 2H), 6.92-6.86 (m, 2H), 6.73 (bs, 1H), 4.07 (dd, 2H, J=6.4 Hz, J=6.4 Hz), 2.90 (dd, 2H, J=6.3 Hz, J=6.3 Hz), 2.67 (q, 4H, J=7.1 Hz), 2.23-1.97 (m, 4H), 1.30-1.07 (m, 4H), 1.08 (t, 6H, J=7.2 Hz), 0.87 (t, 6H, J=7.1 Hz)

(E)-3-(6-chloropyridin-2-yl)-2-cyano-N-(4-(4-(2-(diethylamino)ethoxy)phenyl)heptan-4-yl)acrylamide (WP1735)

Yield 84%. $^1$H NMR (CDCl$_3$, 300 MHz, δ) ppm; 8.13 (s, 1H), 7.76 (dd, 1H, J=J=7.7 Hz), 7.49 (d, 1H, J=7.4 Hz), 7.42 (dd, 1H, J=8.0 Hz, J=0.5 Hz), 7.28-7.20 (m, 2H), 6.92-6.86 (m, 2H), 6.72 (bs, 1H), 4.09 (dd, 2H, J=5.8 Hz, J=5.8 Hz), 2.81 (dd, 2H, J=5.6 Hz, J=5.6 Hz), 2.75-2.40 (m, 4H), 2.30 (s, 3H), 2.20-1.97 (m, 4H), 1.30-1.07 (m, 4H), 0.87 (t, 6H, J=7.4 Hz)

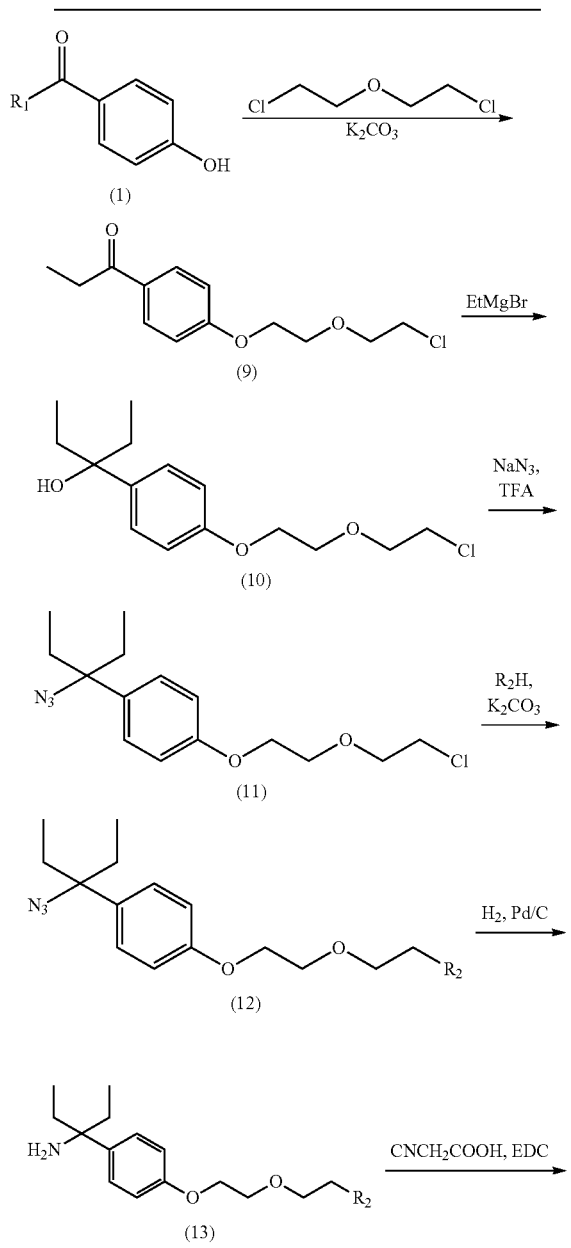

Scheme 2. General synthetic route employed in the synthesis of compounds of type 15, wherein R$_1$ in 1 is ethyl. Compounds WP1723, WP1724, WP1730, WP1731, and WP1732 were synthesize according to the route depicted in Scheme 2.

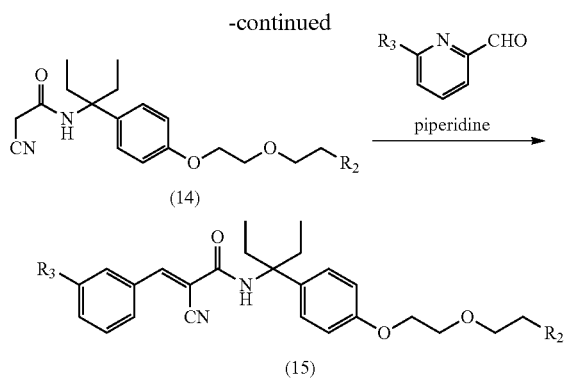

Synthesis of 1-(4-(2-(2-chloroethoxy)ethoxy)phenyl)propan-1-one (9)

Intermediate 9 was obtained according to the literature (Koning et al., 2011). Briefly, a mixture of 4-hydroxypropiophenone (20 mmol), potassium carbonate (33 mmol), KI (2.2 mmol), and 2-chloroethyl ether (20 mL) was prepared and refluxed with vigorous stirring for 48 h. The reaction mixture was diluted with ethyl acetate (50 mL), inorganic salts were removed by filtration, and the filtrate was washed with water before being dried over anhydrous sodium sulfate. The drying agent and solvent were removed, and the crude product was purified by LC. Yield 83.7%. $^1$H NMR (CDCl$_3$, 300 MHz, δ) ppm; 7.98-7.89 (m, 2H), 6.98-6.92 (m, 2H), 4.21 (dd, 2H, J=6.0 Hz, J=4.9 Hz), 3.91 (dd, 2H, J=4.8 Hz, J=4.9 Hz), 3.83 (dd, 2H, J=6.0 Hz, J=5.4 Hz), 3.67 (dd, 2H, J=5.9 Hz, J=5.4 Hz), 2.95 (q, 2H, J=7.3 Hz), 1.21 (t, 3H, J=7.2 Hz)

Synthesis of 3-(4-(2-(2-chloroethoxy)ethoxy)phenyl)pentan-3-ol (10)

Ethylmagnesium bromide (33 mmol) was added dropwise to the vigorously stirred solution of 9 (10 mmol) in THF (80 mL). The resulting mixture was stirred at room temperature for 1 h. After the reaction was judged to be complete by TLC, the reaction mixture was poured into ice-cold 1 N HCl solution (100 mL). After 20 min of stirring product was extracted with ethyl acetate. The organic extract was washed with a 10% solution of sodium bicarbonate, then washed with brine, and the organic extract was dried over anhydrous Na$_2$SO$_4$. The drying agent and solvents were removed, and the crude product was purified by LC using toluene/ethyl acetate gradient for elution. Fractions containing product were pooled together and evaporated to dryness. Yield 86.1%. $^1$H NMR (CDCl$_3$, 300 MHz, δ) ppm; 7.32-7.23 (m, 2H), 6.92-6.85 (m, 2H), 4.14 (dd, 2H, J=6.1 Hz, J=4.9 Hz), 3.94-3.80 (m, 4H), 3.65 (dd, 2H, J=6.1 Hz, J=5.6 Hz), 1.9-1.7 (m, 4H), 1.60 (d, 1H, J=7.1 Hz), 0.75 (t, 3H, J=7.4 Hz)

Synthesis of 1-(3-azidopentan-3-yl)-4-(2-(2-chloroethoxy)ethoxy)benzene (11)

A mixture of compound 3 (8.6 mmol), NaN$_3$ (26 mmol) and chloroform (20 mL) was prepared and vigorously stirred was cooled down to 0° C. Trifluoroacetic acid (43 mmol) was added and the reaction mixture was starred at 0° C. After reaction was judged to be complete by TLC, the mixture was diluted with chloroform (30 mL) and then water (30 mL) was added. The organic and aqueous layers were separated, and organic layer was washed with water and dried. The crude product was purified by column chromatography using a hexanes/ethyl acetate gradient for elution. Fractions containing product were pooled together and evaporated to dryness. Yield 96%. $^1$H NMR (CDCl$_3$, 300 MHz, δ) ppm; 7.27-7.20 (m, 2H), 6.92-6.86 (m, 2H), 4.14 (dd, 2H, J=6.0 Hz, J=4.9 Hz), 3.92-3.80 (m, 4H), 3.66 (dd, 2H, J=6.0 Hz, J=5.6 Hz), 2.3-1.9 (m, 4H), 0.78 (t, 3H, J=7.4 Hz)

Synthesis of Compounds of Type (12)

A mixture of the appropriate compound 11 (2 mmol), the appropriate amine (4.0 mmol), potassium carbonate (20 mmol), and acetonitrile (15 mL) was prepared and the mixture was refluxed with vigorous stirring. After the reaction was judged to be complete by TLC, the reaction mixture was cooled and then diluted with chloroform. Inorganic salts were removed by filtration, solvents were evaporated, and the crude product was purified by LC using a chloroform/methanol gradient for elution. Fractions containing product were pooled together and evaporated to dryness. The following compounds were prepared according to this procedure:

4-(2-(2-(4-(3-azidopentan-3-yl)phenoxy)ethoxy)ethyl)morpholine (12a, R$_1$=Et, R$_2$=morpholino)

Yield 96%. $^1$H NMR (CDCl$_3$, 300 MHz, δ) ppm; 7.27-7.19 (m, 2H), 6.92-6.85 (m, 2H), 4.12 (dd, 2H, J=5.0 Hz, J=4.6 Hz), 3.82 (dd, 2H, J=5.9 Hz, J=5.0 Hz), 3.75-3.67 (m, 4H), 2.67 (dd, 2H, J=5.7 Hz, J=5.7 Hz), 2.54 (dd, 2H, J=4.7 Hz, J=4.6 Hz), 2.3-1.8 (m, 4H), 0.78 (t, 3H, J=7.4 Hz)

1-(2-(2-(4-(3-azidopentan-3-yl)phenoxy)ethoxy)ethyl)-4-methylpiperazine (12b, R$_1$=Et, R$_2$=4-methylpiperazinyl)

Yield 98%. $^1$H NMR (CDCl$_3$, 300 MHz, δ) ppm; 7.25-7.19 (m, 2H), 6.92-6.85 (m, 2H), 4.12 (dd, 2H, J=5.0 Hz, J=4.7 Hz), 3.82 (dd, 2H, J=5.0 Hz, J=5.0 Hz), 3.70 (dd, 2H, J=5.8 Hz, J=5.8 Hz), 2.62 (dd, 2H, J=5.8 Hz, J=5.8 Hz), 2.70-2.33 (m, 8H), 2.27 (s, 3H), 2.3-1.8 (m, 4H), 0.78 (t, 3H, J=7.4 Hz)

Synthesis of Compounds Type (13)

The appropriate compound 12 (1 g) was dissolved in the mixture of THF/EtOH (1:1 v/v, 15 mL). Pd/C (10% wet Degussa type, 100 mg) was added and mixture was exposed to hydrogen gas using a Paar apparatus (40 p.s.i.) overnight. The reaction mixture was filtered through Celite®, the solvents were evaporated, and the crude product was purified by LC using a chloroform/methanol gradient as eluent. Fractions containing product were pooled together and evaporated to dryness. The following compounds were prepared according to this procedure:

3-(4-(2-(2-morpholinoethoxy)ethoxy)phenyl)pentan-3-amine (13a, R$_1$=Et, R$_2$=morpholino)

Yield 89%. $^1$H NMR (CDCl$_3$, 300 MHz, δ) ppm; 7.35-7.27 (m, 2H), 6.90-6.83 (m, 2H), 4.16 (dd, 2H, J=5.1 Hz, J=4.6 Hz), 3.82 (dd, 2H, J=5.8 Hz, J=5.0 Hz), 3.75-3.68 (m, 6H), 2.62 (dd, 2H, J=5.8 Hz, J=5.8 Hz), 2.52 (dd, 4H, J=4.7 Hz, J=4.6 Hz), 1.92-1.65 (m, 4H), 0.74 (t, 3H, J=7.4 Hz)

3-(4-(2-(2-(-4-methylpiperazin-1-yl)ethoxy)ethoxy)phenyl)pentan-3-amine (13b, R$_1$=Et, R$_2$=4-methylpiperazinyl)

Yield 86%. $^1$H NMR (CDCl$_3$, 300 MHz, δ) ppm; 7.32-7.26 (m, 2H), 6.90-6.83 (m, 2H), 4.11 (dd, 2H, J=5.1 Hz, J=4.7 Hz), 3.81 (dd, 2H, J=5.9 Hz, J=4.7 Hz), 3.70 (dd, 2H, J=5.9 Hz, J=5.9 Hz), 2.63 (dd, 2H, J=5.8 Hz, J=5.8 Hz), 2.70-2.33 (m, 8H), 2.27 (s, 3H), 1.88-1.56 (m, 4H), 0.71 (t, 3H, J=7.3 Hz)

Synthesis of Compounds Type (14)

EDC (1.7 mmol) followed by DMAP (0.01 mmol) were added to a solution of the appropriate compound 13 (1.66 mmol) and cyanoacetic acid (3.33 mmol) in DCM (10 mL) and the resulting mixture was stirred at room temperature overnight. The crude product was purified by LC using a chloroform/methanol gradient as eluent. Fractions containing product were pooled together and evaporated to dryness. The following compounds were prepared according to this procedure:

2-cyano-N-(3-(4-(2-(2-morpholinoethoxy)ethoxy)phenyl)pentan-3-yl)acetamide (14a, R$_1$=Et, R$_2$=morpholino)

Yield 65%. $^1$H NMR (CDCl$_3$, 300 MHz, δ) ppm: 7.26-7.17 (m, 2H), 6.93-6.85 (m, 2H), 6.12 (bs, 1H), 4.11 (dd, 2H, J=5.1 Hz, J=4.6 Hz), 3.82 (dd, 2H, J=4.7 Hz, J=5.0 Hz), 3.75-3.66 (m, 6H), 3.34 (s, 2H), 2.61 (dd, 2H, J=5.8 Hz, J=5.8 Hz), 2.51 (dd, 4H, J=4.7 Hz, J=4.6 Hz), 2.20-1.98 (m, 4H), 0.74 (t, 3H, J=7.4 Hz)

2-cyano-N-(3-(4-(2-(2-(4-methylpiperazin-1-yl)ethoxy)ethoxy)phenyl)pentan-3-yl)acetamide (14b, R$_1$=Et, R$_2$=4-methylpiperazinyl)

Yield 83%. $^1$H NMR (CDCl$_3$, 300 MHz, δ) ppm: 7.26-7.17 (m, 2H), 6.92-6.84 (m, 2H), 6.33 (bs, 1H), 4.10 (dd, 2H, J=4.9 Hz, J=3.5 Hz), 3.79 (dd, 2H, J=4.8 Hz, J=6.0 Hz), 3.67 (dd, 2H, J=4.6 Hz, J=5.5 Hz), 3.37 (s, 2H), 2.64 (dd, 2H, J=5.6 Hz, J=5.5 Hz), 2.70-2.46 (m, 8H), 2.36 (s, 3H), 2.20-1.94 (m, 4H), 0.74 (t, 3H, J=7.4 Hz)

Synthesis of Compounds Type (15)

A mixture of the appropriate compound 14 (1 mmol), the appropriate 6-substituted picolinaldehyde (1.2 mmol), piperidine (0.1 mmol), and acetonitrile (20 mL) was prepared and refluxed with stirring. After the reaction was judged to be complete by TLC, the reaction mixture was evaporated to dryness and crude product was purified by LC using a chloroform/methanol gradient as eluent. Fractions containing product were pooled together and evaporated to dryness. The following compounds were prepared according to this procedure:

(E)-3-(6-chloropyridin-2-yl)-2-cyano-N-(3-(4-(2-(2-morpholinoethoxy)ethoxy)phenyl)pentan-3-yl)acrylamide (WP1723)

Yield 68.4%. $^1$H NMR (CDCl$_3$, 300 MHz, δ) ppm; 8.13 (s, 1H), 7.76 (dd, 1H, J=J=7.8 Hz), 7.49 (d, 1H, J=7.3 Hz), 7.43 (dd, 1H, J=8.0 Hz, J=0.6 Hz), 7.30-7.20 (m, 2H), 6.93-6.85 (m, 2H), 6.71 (bs, 1H), 4.11 (dd, 2H, J=5.1 Hz, J=4.6 Hz), 3.81 (dd, 2H, J=4.7 Hz, J=5.0 Hz), 3.74-3.66 (m, 6H), 2.61 (dd, 2H, J=5.7 Hz, J=5.7 Hz), 2.52 (dd, 4H, J=4.7 Hz, J=4.6 Hz), 2.30-2.02 (m, 4H), 0.77 (t, 3H, J=7.3 Hz)

(E)-2-cyano-N-(3-(4-(2-(2-morpholinoethoxy)ethoxy)phenyl)pentan-3-yl)-3-(pyridin-2-yl)acrylamide (WP1724)

Yield 73.5%. $^1$H NMR (CDCl$_3$, 300 MHz, δ) ppm; 8.83 (dd, 1H, J=4.7 Hz, J=0.9 Hz), 8.21 (s, 1H), 7.79 (ddd, 1H, J=J=7.8 Hz, J=1.8 Hz), 7.55 (d, 1H, J=7.8 Hz), 7.39 (ddd, 1H, J=11.6 Hz, J=4.7 Hz, J=1.1 Hz), 7.30-7.23 (m, 2H), 6.93-6.85 (m, 2H), 6.72 (bs, 1H), 4.15 (dd, 2H, J=5.0 Hz, J=4.7 Hz), 3.82 (dd, 2H, J=4.7 Hz, J=5.0 Hz), 3.75-3.65 (m, 6H), 2.61 (dd, 2H, J=5.7 Hz, 0.1=5.7 Hz), 2.52 (dd, 4H, J=4.7 Hz, J=4.6 Hz), 2.30-2.03 (m, 4H), 0.77 (t, 3H, J=7.3 Hz)

(E)-3-(6-chloropyridin-2-yl)-2-cyano-N-(3-(4-(2-(2-(4-methylpiperazin-1-yl)ethoxy)ethoxy)phenyl)pentan-3-yl)acrylamide (WP1731)

Yield 64%. $^1$H NMR (CDCl$_3$, 300 MHz, δ) ppm; 8.13 (s, 1H), 7.77 (dd, 1H, J=J=7.8 Hz), 7.49 (d, 1H, J=7.3 Hz), 7.42 (dd, 1H, J=8.0 Hz, J=0.6 Hz), 7.28-7.20 (m, 2H), 6.98-6.85 (m, 2H), 6.71 (bs, 1H), 4.11 (dd, 2H, J=5.1 Hz, J=4.7 Hz), 3.88 (dd, 2H, J=5.1 Hz, J=4.8 Hz), 3.72-3.65 (m, 4H), 2.88 (dd, 2H, J=4.7 Hz, J=4.7 Hz), 2.62 (dd, 2H, J=5.8 Hz, J=5.8 Hz), 2.70-2.33 (m, 8H), 2.28 (s, 3H), 2.26-2.22 (m, 4H), 0.77 (t, 3H, J=7.4 Hz)

Synthesis of WP1732

A 0.25 M solution of maleic acid in acetonitrile (40 mL) was added to a solution of WP1731 (2.58 g, 4.78 mmol) in acetonitrile (5 mL). Diethyl ether (50 mL) was added and the resulting off-white solid was filtered and washed with diethyl ether to pH ~7. Solid was dried under reduced pressure to give 2.48 g of WP1732. Yield 67%. $^1$H NMR (600 MHz, DMSO, δ) ppm: 8.18 (s, 1H), 8.07 (dd, $^1$H, J=J=7.86 Hz), 8.01 (s, 1H), 7.86 (d, 1H, J=7.44 Hz), 7.68 (d, 1H, J=8.28 Hz), 7.26 (d, 2H, J=8.88 Hz), 6.88 (d, 2H, J=8.8 Hz), 6.15 (s, 4H), 4.09 (dd, 2H, J=4.74 Hz, J=4.38 Hz), 3.74 (dd, 2H, J=J=4.55 Hz), 3.64 (dd, 2H, J=J=5.28 Hz), 3.50-2.80 (m, 8H), 2.74 (bs, 2H), 2.67 (bs, 3H), 2.13 (m, 2H), 1.94 (m, 2H), 0.69 (t, 6H, J=7.32).

Biological Evaluation of Synthesized Caffeic Acid Derivatives i. Cell Cultures

Glioblastoma U87 and pancreatic cancer cell lines, AsPc-1, Panc-1, Colo357-FG and Colo357-L3.6 were maintained in DMEM with 10% fetal bovine serum (FBS), 100 mg/ml streptomycin, and 100 IU/ml penicillin in 5% CO$_2$ at 37° C.

Tumor cell lines were maintained in DMEM with 10% fetal bovine serum (FBS), 100 microg/ml streptomycin, and 100 IU/ml penicillin in 5% CO$_2$ at 37° C.

AsPc-1: A human pancreatic tumor cell line established from the ascites of a patient with histopathologically confirmed adenocarcinoma of the head of the pancreas. See Chen et al. (1982).

Panc-1: An epithelioid cell line started from a human pancreatic carcinoma of ductal cell origin. See Lieber et al. (1975).

Colo357 was derived from a metastasis of a pancreatic adenocarcinoma. See Morgan et al. (1980).

Colo357-FG and Colo357-L3: Colo357-FG, a fast-growing variant produced regional lymph node metastasis in 58% of nude mice after subcutaneous implantation and growth. It also produced hepatic metastasis in 64% and pulmonary metastasis in 43% of nude mice after intrasplenic implantation of tumor cells. See Vezeridis et al. (1990).

Colo357-L3.5 established by sequential passages of a human pancreatic cancer cell line through the nude mouse liver. See Vezeridis et al. (1992).

WM793 human melanoma tumor cell lines were used from different stages of progression and their biological and molecular analyses. See Satyamoorthy et al. (1997).

ii. Cytotoxicity Assay

For the cytotoxicity assays, 1,500 tumor cells were plated into 96-well flat-bottom tissue culture plates in complete medium (see Tables 2 and 3). After 20 hours fresh media containing different concentrations of compounds disclosed herein added. Cell number was counted after 72 hours by using MTS assay (Promega CellTiter AQ Non-Radioactive Cell Proliferation Assay kit, Madison, Wis., USA) by measuring absorbance at 490 nm with a 96-well plate reader. Data are presented as $IC_{50}$ values derived from relative inhibition of proliferation plus SD of eight measurements. The number of cells in the presence of DMSO was taken as 100%.

TABLE 2

Cytotoxicity of WP compounds in tumor cell lines.

| Compound | Cell Lines ($IC_{50}[\mu M]$) | |
| --- | --- | --- |
| | Colo357-FG | MDA-PATC-53 |
| WP 1066 | 2.1 | 2.4 |
| WP 1721 | 1.1 | 1.1 |
| WP 1722 | 1.2 | 1.1 |
| WP 1793 | 0.8 | 1.0 |
| WP 1794 | 0.6 | 0.9 |
| WP 1723 | 1.2 | 1.4 |
| WP 1724 | 2.8 | 3.5 |
| WP 1727 | 2.2 | 3.0 |
| WP 1731 | 1.5 | 1.8 |
| WP 1732 | 2.6 | 1.8 |
| WP 1733 | 0.95 | 1.1 |
| WP 1734 | 1.5 | 1.6 |
| WP 1735 | 1.2 | 1.0 |
| WP 1736 | 1.7 | 2.9 |

TABLE 3

Comparison of cytotoxicity of WP1732 and WP1066.

| Tumor | Cell Lines | $IC_{50}[\mu M]$ | |
| --- | --- | --- | --- |
| | | WP1066 | WP1732 |
| GBM | LNZ-428 | 1.5 | 2.3 |
| GBM | D423 | | 1.4 |
| GBM | D423 enol | | 2.5 |
| GBM | LN319 | | 2.8 |
| GBM | D423 | | 1.4 |
| GBM | D423 enol | | 2.5 |
| GBM | LN319 | | 2.8 |
| GBM | U87MG | 1.7 | 1.8 |
| Panc | Colo357-FG | 2.0 | 2.6 |
| Panc | MDA-PATC-53 | 2.4 | 1.8 |
| Panc | MIA-PaCa-2 | 1.7 | 1.6 |
| Panc | SU.86.86 | 2.5 | 1.5 |
| Panc | MDA-PATC-148 | | 1.9 |
| Panc | MDA-PATC-153 | | 2.6 |
| Panc | MDA-PATC-108 | 2.4 | 1.6 |
| CTCL | HH | 2.3 | 3.2 |
| CTCL | HuT78 | 1.9 | 2.9 |
| Myeloma | HD2 | 1.7 | 3.8 |
| Melanoma | WM35 | 1.3 | 2.3 |
| Melanoma | A375 | 1.5 | 1.1 |
| Melanoma | SK-MEL-28 | 2.0 | 1.8 |
| Melanoma | WM793 | 2.1 | 1.8 |
| Ependymoma | BT-58 | 1.8 | 1.8 |
| Ovarian | Ovcar-5 | 1.7 | 1.7 |
| Prostate | PC3 | 2.3 | 1.4 |
| Breast | 4T1 | 4.4 | 4.5 |
| Breast | 231-MB | 1.2 | 1.5 |
| Breast | 231 | 4.8 | 2.8 |
| Breast | BT483 | 4.2 | 2.3 |

All of the compounds, compositions, and/or methods disclosed and claimed herein can be made and executed without undue experimentation in light of the present disclosure. While the compounds, compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference:

U.S. Pat. No. 6,426,366
U.S. Pat. No. 7,745,468
U.S. Pat. No. 8,143,412
U.S. Pat. No. 8,779,151
U.S. Patent Application Publication 2003/0013748
Alas and Bonavida, *Clin. Cancer Res.,* 9(1):316-26, 2003.
Bharti et al., *J. Immunol.,* 171(7):3863-3871, 2003.
Burdelya et al., *Mol. Cancer Ther.,* 1(11):893-9, 2002.
Catlett-Falcone et al., *Immunity,* 10(1):105-15, 1999.
Constantin et al., *Eur. J. Immunol.,* 28(11):3523-9, 1998.
Kerr et al., *FEBS Lett.,* 546(1):1-5, 2003.
Koning et al., *Toxicol. Lett.* 206(1):54-59, 2011.
Kondo, et al., *Oncogene,* 26(17):2435-44, 2007.
Meydan et al., *Nature,* 379(6566):645-8, 1996.
Reagan-Shaw et al., *FASEB J.,* 22(3):659-661, 2008.
Verma et al., *Cancer Metastasis Rev.,* 22(4):423-34, 2003.
Yu and Jove, *Nature Rev. Cancer,* 4(2):97-105, 2004.

What is claimed is:

1. A compound of the formula:

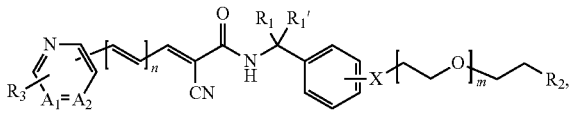

(I)

wherein:
- $A_1$ and $A_2$ are each independently —CH= or —N=, provided that $A_1$ and $A_2$ are not both —N=;
- m is 0-6;
- n is 0, 1, or 2;
- X is O, S, or $NR_4$;
  - wherein $R_4$ is hydrogen, alkyl$_{(C1-6)}$, or substituted alkyl$_{(C1-6)}$;
- $R_1$ and $R_1'$ are each independently $C_{1-8}$-alkyl, $C_{3-8}$-cycloalkyl, —$C_{1-8}$-alkanediyl—$C_{3-8}$-cycloalkyl, $C_{2-8}$-alkenyl, $C_{2-8}$-alkynyl, $C_{6-12}$-aryl, $C_{7-12}$-aralkyl, or a substituted version of any of these groups, or
- $R_1$ and $R_1'$ are taken together and are $C_{2-8}$-alkanediyl or substituted $C_{2-8}$-alkanediyl;
- $R_2$ is $C_{2-12}$-heterocycloalkyl, $C_{2-8}$-dialkylamino, $C_{1-8}$-heteroaryl, $C_{1-8}$-alkylamino, $C_{6-8}$-arylamino, $C_{1-8}$-alkoxy, $C_{6-12}$-aryloxy, or substituted versions of any of these groups; and
- $R_3$ is halo, hydrogen, hydroxy, amino, cyano or mercapto;

or a pharmaceutically acceptable salt thereof.

2. The compound of claim 1, further defined as:

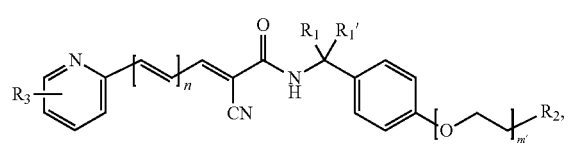

(II)

wherein:
- m' is 1-4;
- n is 0 or 1;
- $R_1$ and $R_1'$ are each independently $C_{1-8}$-alkyl, $C_{3-8}$-cycloalkyl, —$C_{1-8}$-alkanediyl—$C_{3-8}$-cycloalkyl, $C_{2-8}$-alkenyl, $C_{2-8}$-alkynyl, $C_{6-12}$-aryl, $C_{7-12}$-aralkyl, or a substituted version of any of these groups;
- $R_2$ is $C_{2-12}$-heterocycloalkyl, $C_{2-8}$-dialkylamino, $C_{1-8}$-heteroaryl, $C_{1-8}$-alkylamino, $C_{6-8}$-arylamino, $C_{1-8}$-alkoxy, $C_{6-12}$-aryloxy, or substituted versions of any of these groups; and
- $R_3$ is halo, hydrogen, hydroxy, amino, cyano or mercapto;

or a pharmaceutically acceptable salt thereof.

3. The compound of claim 1, further defined as:

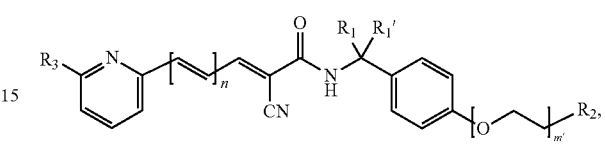

(III)

wherein:
- m' is 1-4;
- n is 0 or 1;
- $R_1$ and $R_1'$ are each independently $C_{1-8}$-alkyl, $C_{3-8}$-cycloalkyl, —$C_{1-8}$-alkanediyl—$C_{3-8}$-cycloalkyl, $C_{2-8}$-alkenyl, $C_{2-8}$-alkenyl, $C_{6-12}$-aryl, $C_{7-12}$-aralkyl, or a substituted version of any of these groups;
- $R_2$ is $C_{2-12}$-heterocycloalkyl, $C_{2-8}$-dialkylamino, $C_{1-8}$-heteroaryl, $C_{1-8}$-alkylamino$_{(C1-8)}$, $C_{6-8}$-arylamino, $C_{1-8}$-alkoxy, $C_{6-12}$-aryloxy, or substituted versions of any of these groups; and
- $R_3$ is halo, hydrogen, hydroxy, amino, cyano or mercapto;

or a pharmaceutically acceptable salt thereof.

4. The compound of claim 2, wherein m' is 1-3.
5. The compound of claim 4, wherein m' is 2.
6. The compound of claim 1, wherein n is 0.
7. The compound of claim 1, wherein $R_1$ is $C_{1-8}$-alkyl.
8. The compound of claim 7, wherein $R_1$ is ethyl.
9. The compound of claim 1, wherein $R_1'$ is $C_{1-8}$-alkyl.
10. The compound of claim 9, wherein $R_1'$ is ethyl.
11. of claim 1, wherein $R_2$ is $C_{2-12}$-heterocycloalkyl or a substituted version thereof.
12. The compound of claim 11, wherein $R_2$ is morpholinyl or 4-methylpiperazin-1-yl.
13. The compound of claim 1, wherein $R_3$ is halo.
14. The compound of claim 13, wherein $R_3$ is chloro.
15. The compound of claim 1, wherein compound is in the form of a pharmaceutically acceptable salt.
16. The compound of claim 15, wherein the pharmaceutically acceptable salt is a maleic acid salt.
17. The compound of claim 1, further defined as:

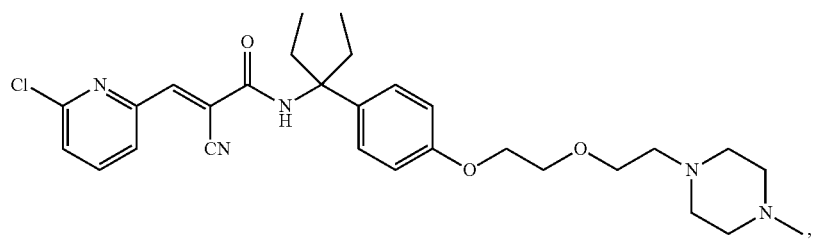

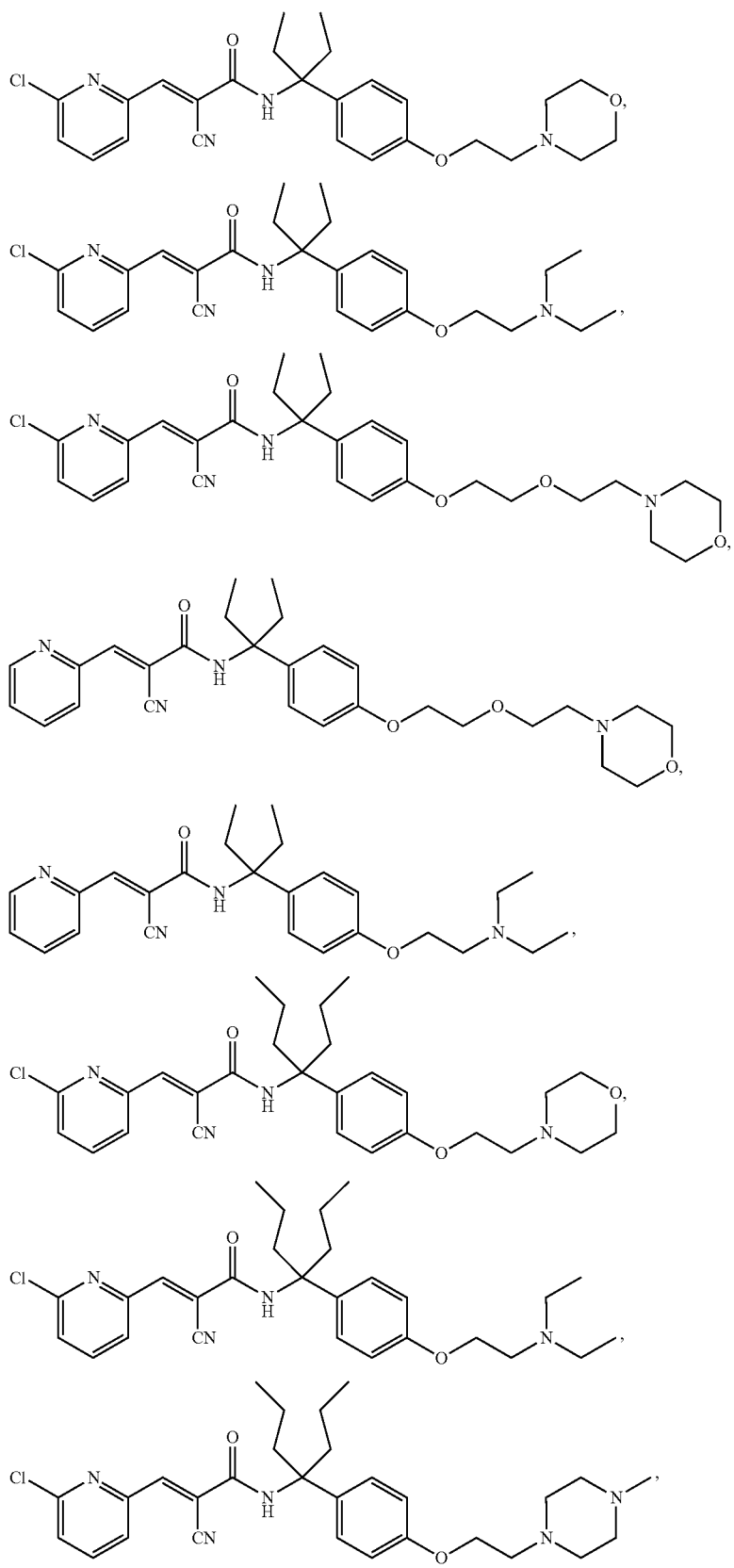

-continued
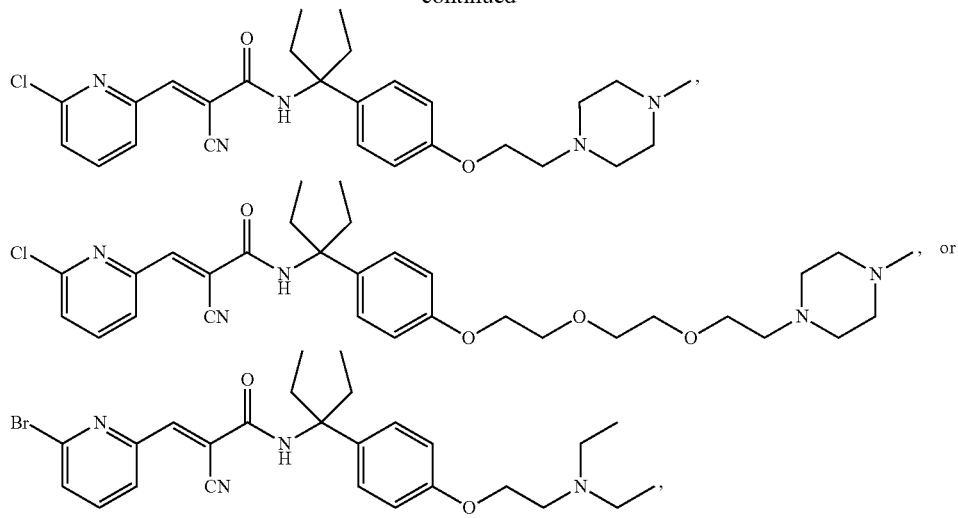
or a pharmaceutically acceptable salt of any of the above formulas.
18. The compound of claim 17 further defined as:
19. A pharmaceutical composition comprising:
a. the compound of claim 1; and
b. an excipient.
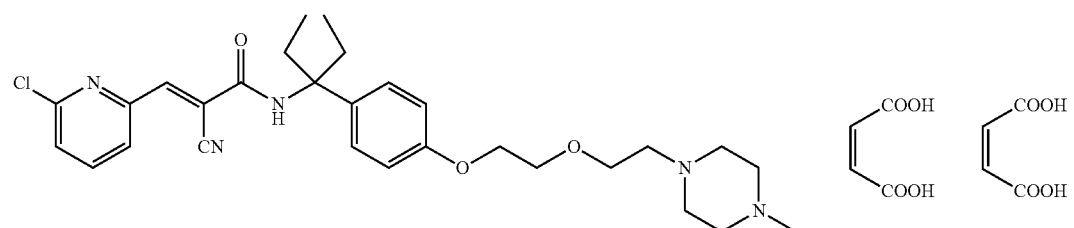
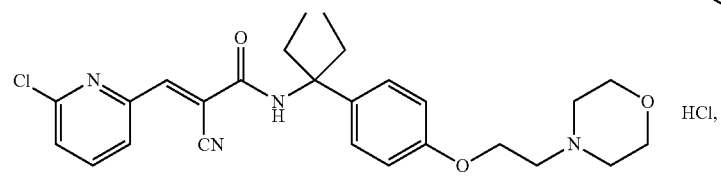
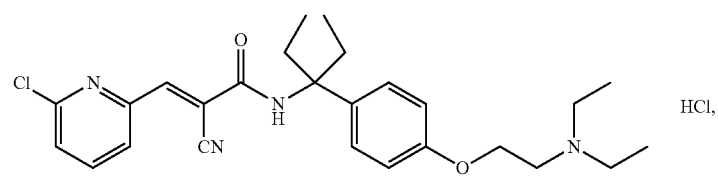
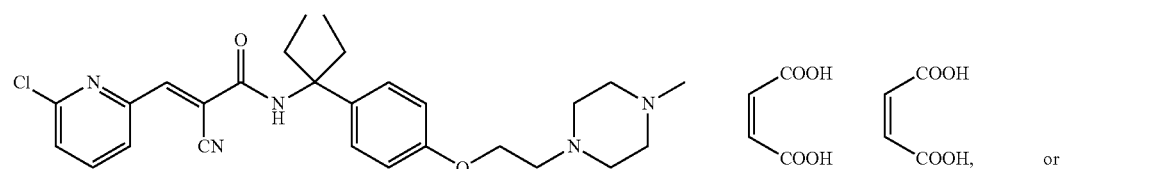
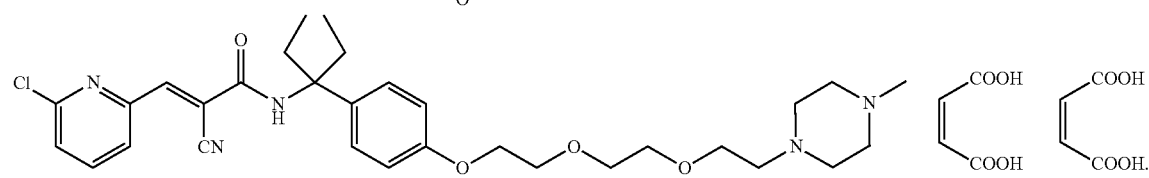

20. A method of treating cancer comprising administering to a patient in need thereof a therapeutically effective amount of a compound of claim 1, wherein the cancer is myeloma, glioblastoma, pancreatic cancer, cutaneous T-cell lymphoma, melanoma, ependymoma, ovarian cancer, prostate cancer, or breast cancer.

21. The method of claim 20, wherein the cancer is of the breast, ovary, pancreas, or prostate.

\* \* \* \* \*

UNITED STATES PATENT AND TRADEMARK OFFICE
CERTIFICATE OF CORRECTION

PATENT NO. : 10,703,721 B2
APPLICATION NO. : 16/185669
DATED : July 7, 2020
INVENTOR(S) : Waldemar Priebe et al.

It is certified that error appears in the above-identified patent and that said Letters Patent is hereby corrected as shown below:

In the Claims

In Claim 3, Column 48, Line 24, delete "$C_{2-8}$-alkenyl, $C_{2-8}$-alkenyl" and insert --$C_{2-8}$-alkenyl, $C_{2-8}$-alkynyl-- therefor.

In Claim 11, Column 48, Line 40, before "of claim 1", insert --The compound--.

Signed and Sealed this
Tenth Day of November, 2020

Andrei Iancu
*Director of the United States Patent and Trademark Office*